United States Patent
Robbins et al.

(10) Patent No.: US 8,273,701 B2
(45) Date of Patent: Sep. 25, 2012

(54) METHOD FOR DIAGNOSING NON-SMALL CELL LUNG CARCINOMA

(75) Inventors: David J. Robbins, Hanover, NH (US); Ziqiang Yuan, Burlington, VT (US); John A. Goetz, Bloomington, IN (US)

(73) Assignee: Trustees of Dartmouth College, Hanover, NH (US)

( * ) Notice: Subject to any disclaimer, the term of this patent is extended or adjusted under 35 U.S.C. 154(b) by 792 days.

(21) Appl. No.: 12/063,781

(22) PCT Filed: Aug. 14, 2006

(86) PCT No.: PCT/US2006/031685
§ 371 (c)(1),
(2), (4) Date: May 26, 2009

(87) PCT Pub. No.: WO2007/027421
PCT Pub. Date: Mar. 8, 2007

(65) Prior Publication Data
US 2010/0029580 A1    Feb. 4, 2010

Related U.S. Application Data

(60) Provisional application No. 60/708,511, filed on Aug. 16, 2005.

(51) Int. Cl.
*A01N 61/00* (2006.01)
(52) U.S. Cl. .......................................................... 514/1
(58) Field of Classification Search .................. None
See application file for complete search history.

(56) References Cited

U.S. PATENT DOCUMENTS 6,291,516 B1    9/2001    Dudek et al.

FOREIGN PATENT DOCUMENTS
WO    02098420    12/2002

OTHER PUBLICATIONS

Taipale et al (Nature, 2001, 411: 349-354).*
Watkins et al (Nature, 2003, 422(6929): 313-317).*
Offiong (Transition Met. Chem., 1997, 22: 263-269).*
Bale et al., "The hedgehog pathway and basal cell carcinomas", Human Molecular Genetics 2001 10(7):757-762.
Berman et al., "Widespread requirement for Hedgehog ligand stimulation in growth of digestive tract tumours", Nature 2003 425:846-851.
Karhadkar et l., "Hedgehog signalling in prostate regeneration, neoplasia and metastasis", Nature 2004 431:707-712.
Murone et al., "Hedgehog Signal Transduction:From Flies to Vetebrates", Exp Cell Res 1999 253:25-33.
Pasca di Magliano et al., Hedgehog signalling in cancer formation and maintenance, Nat Rev Cancer 2003 3:903-911.
Ruiz et al., "Gli proteins and Hedgehog signaling", Trends genet 1999 15:418-425.
Taipale et al., "The Hedgehog and Wnt signalling pathways in cancer", Nature 2001 411:349-354.
Watkins et al., "Hedgehog signalling in foregut malignancy", Biochem Pharmacol 2004 68:1055-1060.

* cited by examiner

*Primary Examiner* — Sean Aeder
(74) *Attorney, Agent, or Firm* — Licata & Tyrrell P.C.

(57) ABSTRACT

The present invention relates to the constitutive activity of the Hedgehog pathway in non-small cell lung carcinoma (NSCLC). A method for diagnosing NSCLC by detecting the level of a component of the Hedgehog pathway is provided, as is a method for identifying subjects that will respond positively to treatment with a Hedgehog pathway antagonist. Methods for treating subjects with cancer or cancers resistant to Hedgehog pathway antagonists are also provided.

1 Claim, No Drawings

METHOD FOR DIAGNOSING NON-SMALL CELL LUNG CARCINOMA

This application claims benefit of U.S. Provisional Patent Application Ser. No. 60/708,511, filed Aug. 16, 2005, the content of which is incorporated herein by reference in its entirety.

This invention was made in the course of research sponsored by the National Institutes of Health, Grant No. GM 064011. The U.S. government may have certain rights in this invention.

BACKGROUND OF THE INVENTION

The Hedgehog signaling pathway composed of the human genes Sonic Hedgehog (Shh) and Indian Hedgehog, collectively referred to herein as Hedgehog, as well as Patched (Ptc), Smoothened (Smo), Suppressor Of Fused [Su(Fu)] and Gli1, has been implicated in the pathogenesis of certain cancers (Bale & Yu (2001) *Hum. Mol. Genet.* 10:757-62; Pasca di Magliano & Hebrok (2003) *Nat. Rev. Cancer* 3:903-11; Ruiz i Altaba (1999) *Trends Genet.* 15:418-25; Taipale & Beachy (2001) *Nature* 411:349-54; Murone, et al. (1999) *Exp. Cell Res.* 253:25-33), consistent with its substantial role in regulating both cellular proliferation and cell fate determination during development (Ogden, et al. (2004) *Biochem. Pharmacol.* 67:805-14).

Hedgehog signaling is engaged when Hedgehog binds to its receptor Ptc. In the absence of Hedgehog, Ptc is required to keep the Hedgehog pathway in an off state. Thus, Hedgehog binding relieves the negative action of its receptor (Ogden, et al. (2004) supra). Ptc expression is induced in response to Hedgehog, and increased Ptc tethers Hedgehog to responsive cells, limiting the distribution of the ligand via a negative-feedback mechanism. Ptc normally inhibits the seven transmembrane domain protein, Smo, which is required for all aspects of Hedgehog signaling (Ogden, et al. (2004) supra). Smo has some identity to the guanine nucleotide binding protein coupled receptor superfamily, and is classified as a member of the Frizzled family. Smo activates the Hedgehog pathway by affecting the activity of members of the Gli family of transcription factors, Gli1-3. Gli2 and Gli3 are most related, based on primary sequence and function, and mice lacking Gli2 or Gli3 have severe developmental abnormalities. The precise role of Gli1 in Hedgehog signaling is unknown, as mice lacking Gli1 exhibit no obvious phenotype. Thus, it has been proposed that Gli1 may not be a direct regulator of the Hedgehog pathway, as Gli2 and Gli3 appear to be, but is involved in a feedback or maintenance program, which allows Hedgehog signaling in a Hedgehog-independent fashion. This suggestion is consistent with the observation that Gli1 is a Hedgehog target gene (Lee, et al. (1997) *Development* 124:2537-52) and with the role Gli1 plays in human oncogenesis, in which tumor cell proliferation is blocked when Gli1 levels are reduced (Ruiz i Altaba (1999) supra; Sanchez, et al. (2004) *Proc. Natl. Acad. Sci. USA* 101:12561-6; Dahmane, et al. (1997) *Nature* 389:875-81; Grachtchouk, et al. (2000) *Nat. Genet.* 24:216-7).

Individuals suffering from the rare inherited developmental disorder known as Gorlin's syndrome (Hahn, et al. (1996) *Cell* 85:841-51; Hahn, et al. (1996) *J. Biol. Chem.* 271:12125-8; Johnson, et al. (1996) *Science* 272:1668-71) not only have developmental defects, but also have an inherited predisposition to basal cell carcinoma (BCC), rhabdomyosarcoma and medulloblastoma. Mutations in this inherited disorder map to the Ptc gene, which encodes the Hedgehog receptor. The loss-of-function mutations found in both hereditary and sporadic cases of BCC implicate Ptc as a tumor suppressor in this common human cancer (Bale & Yu (2001) supra; Quinn & Epstein (2003) *Methods Mol. Biol.* 222:85-95). Consistent with the critical role of Ptc as a tumor suppressor, mice heterozygous for Ptc develop a similar spectrum of cancers as Gorlin's syndrome patients (Goodrich, et al. (1997) *Science* 277:1109-13). Other components of the Hedgehog pathway, such as the gene encoding Smo, are also often mutated in sporadic forms of these same malignancies, further suggesting a role of the Hedgehog signaling pathway in certain human cancer (Xie, et al. (1998) *Nature* 391:90-2).

Constitutive activation of the Hedgehog pathway has been detected in non-small cell lung carcinoma tissue (NSCLC; Watkins & Peacock (2004) *Biochem. Pharmacol.* 68:1055-60) and implicated as a required event in other human cancers, including breast cancer, prostate cancer, pancreatic cancer and small cell lung carcinoma (SCLC) (Lewis (2001) *J. Mammary Gland Biol. Neoplasia* 6:53-66; Vorechovsky, et al. (1999) *Eur. J. Cancer* 35:711-3; Kubo, et al. (2004) *Cancer Res.* 64:6071-4; Berman, et al. (2003) *Nature* 425:846-51; Watkins & Peacock (2004) supra; Fan, et al. (2004) *Endocrinology* 145:3961-70; Karhadkar, et al. (2004) *Nature* 431:707-12; Sanchez, et al. (2004) supra; Sheng, et al. (2004) *Mol. Cancer.* 3:29). In the tumors examined, no mutations of Ptc or Smo were found. Instead, increased production of Hedgehog, in an autocrine fashion, was implicated in tumor maintenance. In these tumor cells, Hedgehog is required as a mitogen (Watkins, et al. (2003) *Nature* 422:313-7; Karhadkar, et al. (2004) supra; Sanchez, et al. (2004) supra; Berman, et al. (2002) *Science* 297:1559-61). Additionally, hyper-activation of Hedgehog signaling has been found to act as a reliable marker of clinically aggressive human tumors (Karhadkar, et al. (2004) supra). Many cell lines of these tumors appear to require Hedgehog signaling for their survival, as the addition of Hedgehog pathway antagonists confers tumor cell apoptosis. Similar results were obtained when mice carrying xenografts of various human tumors were treated with Hedgehog pathway antagonists (Berman, et al. (2003) supra; Karhadkar, et al. (2004) supra). Furthermore, after the tumor regressed it did not reappear after completion of the treatment.

SUMMARY OF THE INVENTION

The present invention is a method for diagnosing a non-small cell lung carcinoma. The method involves detecting in a sample from a subject suspected of having or at risk of having non-small cell lung carcinoma an elevated level of a component of the Hedgehog pathway as compared to a normal sample thereby diagnosing non-small cell lung carcinoma in the subject.

The present invention is also a method for determining sensitivity of a patient with a cancer to treatment with an antagonist of the Hedgehog pathway. This method of the invention involves obtaining a tumor sample from a patient with a cancer in which tumor cell proliferation is dependent upon the Hedgehog pathway, detecting in the tumor sample the level of expression of a selected biomarker associated with sensitivity to a Hedgehog pathway antagonist and comparing the detected level to a control level, wherein the compared level is indicative of the sensitivity of the patient to treatment with a Hedgehog pathway antagonist.

The present invention is further a method for treating non-small cell lung carcinoma in a patient with tumor cells that are resistant to Hedgehog pathway antagonists. The method of treatment involves administering to a patient with non-small cell lung carcinoma tumor cells that are resistant to Hedgehog pathway antagonists, an inhibitor of Gli1 in combination with a Hedgehog pathway antagonist thereby treating the non-small cell lung carcinoma in the patient.

The present invention is also a method for decreasing proliferation of a tumor cell. The method involves contacting a tumor cell which is dependent upon the Hedgehog pathway for proliferation an effective amount of Compound 1, Compound 2, Compound 3, Compound 4, Compound 5, Compound 6, Compound 7, Compound 8, Compound 9, or Compound 10, or derivatives or analogs thereof, so that proliferation of the tumor cell is decreased.

Further, the present invention is a method for treating a cancer in which tumor cell proliferation is dependent upon the Hedgehog pathway. The method involves administering to a patient having a cancer dependent upon Hedgehog pathway signaling an effective amount of Compound 1, Compound 2, Compound 3, Compound 4, Compound 5, Compound 6, Compound 7, Compound 8, Compound 9, or Compound 10, or derivatives or analogs thereof, so that at least one sign or symptom of the cancer is reduced.

DETAILED DESCRIPTION OF THE INVENTION

Lung cancer is the most common cause of cancer in men and women in the United States, with more than 150,000 deaths annually, and an overall five-year survival of only 14% (Landis, et al. (1999) *CA Cancer J. Clin.* 49:8-31). Lung cancer can be divided into two distinct classes, non-small cell lung carcinoma (NSCLC) and small cell lung carcinoma (SCLC) (Minna, et al. (2002) *Cancer Cell* 1:49-52). While constitutive Hedgehog signaling has been demonstrated in SCLC (Watkins, et al. (2003) supra), SCLC represents only 20% of all lung cancers. It has now been found that the Hedgehog pathway is constitutively active in a subset of NSCLC. As this is the most common form of lung cancer, a decrease in the prevalence of this cancer would affect the mortality and morbidity of a large number of people.

The results disclosed herein indicate that NSCLC can be classified into three distinct subtypes, those that do not require Hedgehog activity, those that require Hedgehog activity and are sensitive to known Hedgehog inhibitors and those that require Hedgehog activity but are insensitive to known Hedgehog inhibitors. Further, a molecular pharmacological marker of the Hedgehog pathway has been identified that is predictive of Hedgehog-dependent NSCLC cases that are not likely to respond to known Hedgehog pathway antagonists.

To demonstrate the involvement of the Hedgehog pathway in the pathogenesis of various cancers, a panel of 60 well-characterized human cancer cells lines (NCI-60) from the Developmental Therapeutics Program (DTP) at the National Cancer Institute (Weinstein, et al. (1997) *Science* 275:343-9) was screened with the known Smo antagonist SANT1.

The NCI-60 panel of cell lines includes cells derived from melanoma, leukemia, and cancers of the lung, central nervous system, kidney, ovary, colon, breast and prostate. Advantageously, the NCI-60 panel has been screened with a plurality of compounds with the drug concentration resulting in 50% growth inhibition ($GI_{50}$ determined for each cell line, so that a distinct "fingerprint" signature has been created for each small-molecule tested. Further, DNA microarray analyses have been performed on the NCI-60 panel, allowing for gene expression profile comparisons between drug-sensitive cell lines and drug-insensitive cell lines in response to a particular agent.

Results from the NCI-60 panel screen highlighted the important role that the Hedgehog pathway plays in breast and prostate cancer (Table 1). Furthermore, this screen indicated that ovarian tumors and nearly 75% of the NSCLC cell lines also required Hedgehog activity for proliferation. These findings underscore the broad importance of Hedgehog signaling in carcinogenesis.

TABLE 1

| Cancer | Cell Line | $-\log [GI_{50}]$ |
| --- | --- | --- |
| Leukemia | HL-60 | 4.54 |
| | K-562 | 4.51 |
| | MOLT-4 | 4.57 |
| | RPMI-8226 | 4.70 |
| | SR | 4.86 |
| NSCLC | A549 | 4.00 |
| | EKVX | 4.00 |
| | HOP62 | 4.79 |
| | NCI-H226 | 4.56 |
| | NCI-H23 | 4.38 |
| | NCI-H322M | 5.08 |
| | NCI-H460 | 4.47 |
| | NCI-H522 | 4.11 |
| Colon | COLO 205 | 4.39 |
| | HCT-116 | 4.55 |
| | HCT-15 | 4.52 |
| | HT29 | 4.37 |
| | KM12 | 4.50 |
| | SW-620 | 4.00 |
| Central Nervous System | SF-268 | 4.42 |
| | SF-295 | 4.00 |
| | SF-539 | 4.12 |
| | SNB-19 | 4.00 |
| | SNB-75 | 4.00 |
| | U251 | 4.17 |
| Melanoma | LOX IMVI | 4.36 |
| | SK-MEL-2 | 4.22 |
| | SK-MEL-28 | 4.09 |
| | SK-MEL-5 | 4.73 |
| | UACC-257 | 4.20 |
| | UACC-62 | 4.47 |
| Ovarian | IGROV1 | 5.08 |
| | OVCAR-5 | 4.00 |
| | OVCAR-8 | 4.00 |
| Renal | 786-0 | 4.64 |
| | ACHN | 4.28 |
| | CAKI-1 | 4.00 |
| | RXF 393 | 4.00 |
| | SN12C | 4.00 |
| | TK-10 | 4.54 |
| | UO-31 | 4.18 |
| Prostate | PC-3 | 4.60 |
| | DU-145 | 4.02 |
| Breast | MCF7 | 4.51 |
| | NCI/ADR-RES | 4.30 |
| | MDA-MB-231/ATCC | 4.65 |
| | HS 578T | 4.00 |
| | MDA MB-435 | 4.00 |
| | BT-549 | 4.32 |

Results from DTP analysis of the NCI-60 screen were independently validated with each cell line to determine which NSCLC cell lines required Hedgehog activity to proliferate. In verifying these results, cyclopamine was used instead of SANT1, as cyclopamine is a structurally distinct Hedgehog inhibitor that has the same cellular target as SANT1 (Chen, et al. (2002) *Proc. Natl. Acad. Sci. USA* 99:14071-6). Six NSCLC cell lines (HOP62, A549, NCI-H322M, NCI-H23, NCI-H522, and EKVX) were treated with different concentrations of cyclopamine (5, 10, 15, 20, 25 AM) and cell proliferation was measured 72 hours later. The data was normalized to that of cells treated with similar amounts of tomatidine, a structural analog of cyclopamine used as a negative control (Cooper, et al. (1998) *Science* 280:1603-7). The use of cyclopamine to confirm the SANT1 results provided a more stringent screen for Hedgehog-dependent tumor cells, by establishing that the various SANT1-sensitive cell lines (i.e., HOP62 and NCIH322M) were also sensitive to this second Hedgehog antagonist. This more stringent analysis validated that SANT1/cyclopamine-sensitive NSCLC cell lines were dependent on Hedgehog for growth.

Using the "fingerprint" generated by analysis of SANT1 on the NCI-60 panel, a comparison between the SANT1 fingerprint and the fingerprint generated by other compounds screened on the NCI-60 panel was conducted to identify novel inhibitors of the Hedgehog signaling pathway which can be useful for the treatment of NSCLC and other cancers dependent upon Hedgehog signaling. This comparison identified ten lead compounds which exhibited the same pattern of anti-proliferative activity on the NCI-60 cell lines as SANT1 (Table 2).

TABLE 2

| Compound | NSC Number (CAS Number) | Chemical Structure (Chemical Name) |
|---|---|---|
| 1 | 724383 (147666-90-6) | 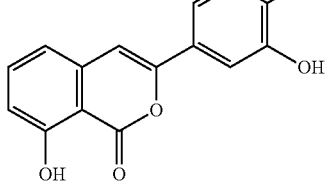 3-(3,4-dihydroxyphenyl)-8-hydroxyisocoumarin (Thunberginol A) |
| 2 | 685927 | 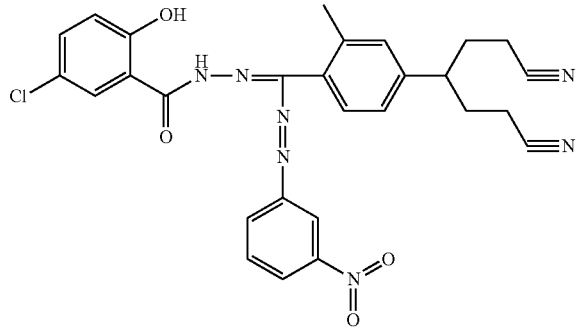 |
| 3 | 685926 | 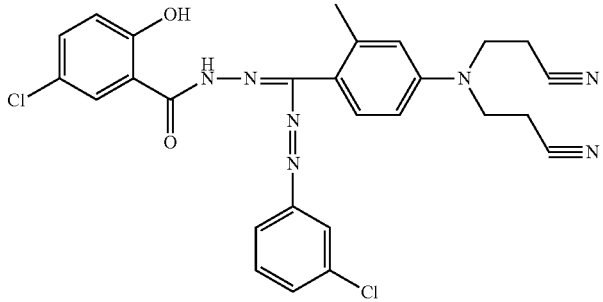 |
| 4 | 608429 | 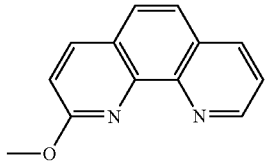 |
| 5 | 692367 | 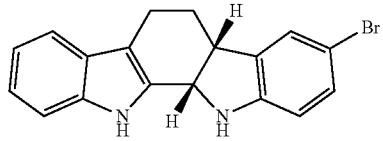 |

TABLE 2-continued

| Compound | NSC Number (CAS Number) | Chemical Structure (Chemical Name) |
|---|---|---|
| 6 | 668332 | |
| 7 | 668301 | |
| 8 | 689869 | |
| 9 | 697593 | |
| 10 | 359464 | |

To further analyze the activity of these compounds, reporter assays were conducted using Shh-Light2 cells, an NIH-3T3-derived cell line containing an integrated Gli-luciferase reporter construct in which expression of the luciferase gene is driven by Gli DNA-binding sites. In this assay, Shh-Light2 cells were plated in triplicate in a 96-well plate for 24 hours followed by 24 hour co-treatment with Shh-conditioned media and various concentrations of test compound. Luciferase activity in the presence of the test compound was then normalized to an internal *Renilla* control. The results of this analysis are presented in Table 3 as percentage of controls (i.e., cells treated with DMSO and conditioned media).

TABLE 3

| Compound | Concentration (M) | | | |
| --- | --- | --- | --- | --- |
| | −9 | −8 | −7 | −6 |
| Cyclopamine | 87 | 91 | 71 | 13 |
| Tomatidine | 93 | 98 | 88 | 98 |
| NSC685926 | 86 | 94 | 89 | 85 |
| NSC608429 | 85 | 74 | 78 | 101 |
| NSC668332 | 108 | 100 | 75 | 33 |
| NSC359464 | 86 | 77 | 72 | 79 |

Given the dose-dependent activity exhibited by NSC668332, it was determined whether derivatives of NSC668332 (Table 4) could also inhibit expression under the same assay conditions above. Luciferase activity for cells exposed to NSC668332 and its derivatives is presented as percentage of controls in Table 5.

TABLE 4

| Compound | NSC Number (CAS Number) | Chemical Structure (Chemical Name) |
| --- | --- | --- |
| 6 | NSC668332 | |
| 11 | NSC668333 | |
| 12 | NSC668326 | |
| 13 | NSC668328 | |
| 14 | NSC668334 | |
| 15 | NSC668336 | |

TABLE 5

| Compound | Concentration (M) | | | |
| --- | --- | --- | --- | --- |
| | −8 | −7 | −6.3 | −6 |
| NSC668332 | 100 | 75 | 35 | 33 |
| NSC668333 | 117 | 79 | 26 | 34 |
| NSC668326 | 93 | 67 | 28 | 9 |
| NSC668328 | 106 | 72 | 25 | 10 |
| NSC668334 | 107 | 66 | 54 | 47 |
| NSC668336 | 96 | 66 | 32 | 32 |

These data demonstrate that potent inhibition of Hedgehog signaling can effectively be achieved using a compound of Formula I

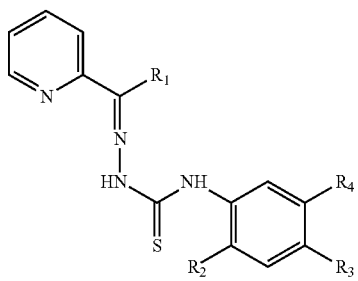

Formula I wherein $R_1$ is an $C_1$-$C_4$ alkyl, $C_6$-$C_{10}$ aryl or $C_3$-$C_8$ cycloalkyl; $R_2$ is hydrogen, halogen (e.g., Cl, F, Br, I), or $C_1$-$C_4$ alkyl; and $R_3$ and $R_4$ are independently hydrogen or $C_1$-$C_4$ alkyl.

RT-PCR analyses were also performed to identify key Hedgehog-dependent target genes across three of the NSCLC cell lines (A549, HOP62 and NCI-H322M). Shh, Gli1, Ptch, and Smo were amplified using the following sets of primers: Shh, sense 5'-gga gtc tct gca cta cga g-3' (SEQ ID NO:1) and antisense 5'-gtc gct gta gag cag ccg-3' (SEQ ID NO:2); Gli1, sense 5'-agt agc tat ggc gag ccc t-3' (SEQ ID NO:3) and antisense 5'-tag gag cct cct gga gat gt-3' (SEQ ID NO:4); Ptch, sense 5'-ctt cgc tct gga gca gat tt-3' (SEQ ID NO:5) and antisense 5'-cag gac att agc acc ttc t-3' (SEQ ID NO:6); and Smo, sense 5'-caa cct gtt tgc cat gtt tgg a-3' (SEQ ID NO:7) and antisense 5'-ctg tgt cca tca ggt tgg tg-3' (SEQ ID NO:8). Gli1 was included in this analysis because the expression of Gli1 has been shown to be important in Hedgehog-dependent tumor cell lines. The three cell lines examined all expressed Hedgehog, as well as various Hedgehog target genes (i.e., Ptc, Gli1, and Smo). Unexpectedly, the A549 cells, which were relatively insensitive to cyclopamine, expressed at least two Hedgehog target genes. Furthermore, this cell line appeared to express Gli1 at a higher level than the NSCLC cell lines that were sensitive to cyclopamine. It has been suggested that some prostate tumor cell lines display hyper-activated Hedgehog signaling, and that this hyper-activation is directly linked to an increased aggressiveness of the tumor cell line (Karhadkar, et al. (2004) supra). Thus, there are at least three classes of NSCLC tumor cell lines, ones in which Hedgehog activity is not required for proliferation (No-Gli), ones in which Hedgehog activity is required for proliferation (Low-Gli) and ones in which the Hedgehog pathway is hyper-activated (High-Gli), resulting in high Gli1 expression and resistance to Hedgehog pathway antagonists.

To further demonstrate the role of Gli1 in NSCLC, Low-Gli NSCLC cell line HOP62 and High-Gli NSCLC cell line A549 were transfected with a Hedgehog reporter gene, in which eight Gli DNA binding sites drive luciferase expression. High-Gli cell lines, which were relatively cyclopamine-resistant, expressed much higher levels of luciferase activity than did the Low-Gli cell lines. This indicated that High-Gli cells were cyclopamine insensitive because Gli1 acts downstream of the cyclopamine target Smo. Thus, reducing the levels of Gli1 in the High-Gli cells could reconstitute sensitivity of these cells to cyclopamine. Accordingly, siRNA 5'-AAC UCC ACA GGC AUA CAG GAU-3' (SEQ ID NO:9) having the desired Gli1 knock-down activity (Sanchez, et al. (2004) supra), was used to reduce Gli1 levels approximately 90% in A549 cells. Notably, when the A549 cell line was transfected with siRNA for 30 hours, treated with different doses of cyclopamine, and cell proliferation measured 48 hours later, the High-Gli cell line exhibited cyclopamine sensitivity. As a control, the High-Gli cell line was also treated with a random siRNA, followed by cyclopamine treatment. These control cells continued to express high levels of Gli1 mRNA and remained relatively cyclopamine-insensitive, demonstrating the specificity of the knock-down siRNA for Gli1.

Furthermore, a correlation was observed between inhibition of cellular proliferation and inhibition of Hedgehog reporter gene activity. This relationship was also a reliable predictor that cyclopamine was exerting its growth attenuating effects through inhibition of Hedgehog signaling, and not through some non-specific, off-target effect. Moreover, cyclopamine was found to have less growth inhibitory activity in the cyclopamine-sensitive NSCLC cell line HOP62 transfected with Gli1 (at an efficiency of approximately 25%) than in HOP62 cells expressing an insertless expression vector.

Given that different NSCLC cell lines exhibit distinct patterns of Gli1 expression, the DTP gene expression profile database was queried revealing that many cyclopamine-insensitive NSCLC cell lines A549, NCI-H23, and NCI-H322M expressed Gli1 at levels 10-20 times higher than cyclopamine-sensitive cell lines. Thus, by two independent determinations, i.e., RT-PCR analysis and the DTP DNA microarray analysis, Gli1 levels were found substantially higher in NSCLC cell lines that were insensitive to Hedgehog antagonists. The Hedgehog reporter gene activity of one of these High-Gli cell lines, A549, was statistically significantly higher than a Low-Gli, or a No-Gli cell line, verifying the presence of higher constitutive Hedgehog activity.

Gene expression analyses of NSCLC cell lines, including A549, have indicated that Gli1 is not activated (Watkins & Peacock (2004) supra). In contrast to these findings, it was found that Gli1 was activated in NSCLC cell line A549. Accordingly, a systematic, matched set comparison of ressected tumor and normal lung tissue from patients with NSCLC was conducted to analyze the expression of Hedgehog pathway components in vivo. Based upon RT-PCR analyses, Shh, Gli1, Ptch, and Smo were elevated in NSCLC tumor tissue compared to normal tissue from the same patients. From these data it was determined that the Hedgehog pathway is activated in 50-60% of patients with NSCLC.

Gene expression profiles of cyclopamine-sensitive tumor cell lines (Hop62, NCI-322M, IGROV1, PC-3, MCF7, MDA-MB-231/ATCC) and cyclopamine-insensitive tumor cell lines (EKVX, OVCAR-5, OVCAR-8, SW-620, HS 578T, MDA-MB-435) were compared to identify additional Hedgehog pathway-associated biomarkers for predicting sensitivity to a Hedgehog antagonist treatment regime. Biomarkers found to be differentially regulated in these tumor cell lines are listed in Table 6.

TABLE 6

| IMAGE Number | Gene ID | Gene Function |
|---|---|---|
| 37469 | Unknown | Unknown |
| 51104 | Unknown | Unknown |
| 53347 | MEIS1 | Homeobox Protein |
| 128329 | FADS2 | Fatty acid Desaturase |
| 143059 | KITLG | Hematopoetic Growth Factor |
| 278375 | 6PF2K | Phosphofructo Kinase |
| 281199 | GS2 | Phospholipase |
| 289818 | MMSDH | Methylmalonate Semialdehyde Dehydrogenase |
| 292118 | PPT2 | Palmitoyl Protein Thioesterase |
| 292320 | FLJ10977 | Unknown |
| 301487 | DEC | basic Helix-Loop-Helix Protein |
| 321997 | TDG | Thymine DNA glycosylase |

TABLE 6-continued

| IMAGE Number | Gene ID | Gene Function |
|---|---|---|
| 323204 | PIM-3 | Serine-Threonine Kinase |
| 344786 | PARP-4 | Poly ADP-ribose Polymersase 4 (W74713) |
| 362059 | LAMA3 | Lamanin alpha 3 |
| 366960 | E6TP1 | E6 Tagrgeted Protein 1 |
| 376296 | TROP-2 | Glycoprotein |
| 416755 | ZIP14 | Zinc transporter |
| 417084 | Vasohibin | Angiogenesis Inhibitor |
| 427845 | ZFP 261 | Zinc Finger Protein 261 |
| 429352 | KIAA1162 | Thioredoxin-Like Protein |
| 469722 | SVCT2 | Sodium-dependent Vitamin C Transporter 2 |
| 470670 | LL5A | Pleckstrin Homology-like Domain, Family B |
| 486356 | HPF1 | Zinc Finger Protein 83 |
| 487100 | HYA22 | CTD Phosphatase 3 |
| 488702 | PREP | Putative Progesterone Binding Protein |
| 488779 | PTK9 | Protein Tyrosine Kinase |
| 509477 | p54/58N | Prolyl Endopeptidase |
| 510301 | GLNRS | Glutaminyl-tRNA Synthetase |
| 510377 | TXNRD1 | Thioredoxin Reductase |
| 510482 | SSBP3 | Single Stranded DNA Binding Protein 3 |
| 510505 | ILGF2 | Insulin-like Growth Factor 2 Receptor |

Collectively, these results demonstrate that Hedgehog signaling is critical for tumor cell proliferation, particularly NSCLC; agents which have a similar anti-proliferation fingerprint as SANT1 can be used to inhibit tumor cell proliferation; that NSCLC can be divided into three subtypes, No-Gli, Low-Gli and High-Gli which are indicative of sensitivity to Hedgehog pathway antagonists; Gli1 overexpression confers Hedgehog pathway antagonist resistance to NSCLC cells; and a plurality of biomarkers exist for distinguishing between tumor cells which are resistant or sensitive to Hedgehog pathway antagonists. Accordingly, the present invention relates to methods of diagnosing NSCLC, identifying cancer patients who will positively respond to treatment with Hedgehog pathway antagonists, agents for treating cancers that are dependent upon Hedgehog pathway signaling and treating NSCLC patients who exhibit resistance to Hedgehog pathway antagonists.

In general, diagnosis of NSCLC involves obtaining a sample of lung tissue, particularly lung tumor tissue (e.g., a biopsy sample, tissue or cell), from a subject suspected of having or at risk of having NSCLC, and determining whether there are detectable, elevated levels of one or more components of the Hedgehog pathway in the sample as compared to, for example, normal lung tissue from the subject or a control sample. Elevated levels of the one or more components of the Hedgehog pathway in the sample as compared to the control is indicative of NSCLC in the subject.

A subject suspected of having NSCLC is one exhibiting signs and symptoms associated with NSCLC (e.g., cough, bloody sputum, shortness of breath, wheezing, chest pain, loss of appetite, unintentional weight loss, weakness, swallowing difficulties, nail abnormalities, joint pain, hoarseness, facial swelling, or bone pain) for which confirmation of NSCLC is desired to select a suitable therapeutic regime. Subjects at risk of having NSCLC include individuals that smoke or have been exposed to second-hand smoke or high levels of pollution, radiation, or asbestos for which routine monitoring is desired for early detection and treatment.

Elevated levels of a component of the Hedgehog pathway can be detected using a variety of well-established methods, including RNA transcript- or protein-based assays. To detect an RNA transcript encoding a component of the Hedgehog pathway, nucleic acids can be directed detected or isolated from the whole sample. Alternatively, the sample can be microdissected to isolate tumor cells from the normal cells present in the sample, with nucleic acids isolated from each cell type for subsequent analysis. The nucleic acid can be whole cell RNA or poly-A+ fractionated. It may also be desired to convert the RNA to a complementary DNA (cDNA) for ease of manipulation and amplification. Methods for isolating, fractionating and amplifying nucleic acids from biological samples is well-known in the art. See, e.g., Sambrook and Russell (2001) supra and other standard laboratory molecular biology protocol manuals.

A variety of methods can be used to evaluate or quantitate the level of RNA transcript encoding a component of the Hedgehog pathway present in the sample. For example, levels of RNA transcript can be evaluated using well-known methods such as northern blot analysis (see, e.g., Sambrook and Russell (2001) supra); oligonucleotide or cDNA fragment hybridization wherein the oligonucleotide or cDNA is configured in an array on a chip or wafer; RNase protection analysis; or RT-PCR, as exemplified herein.

As used herein a component of the Hedgehog pathway is intended to include Sonic Hedgehog (Shh), Indian Hedgehog, Patched (Ptc), Smoothened (Smo), Suppressor Of Fused [Su(Fu)] and Gli1. Suitable primers, probes, or oligonucleotides useful for detection of the transcript encoding these components are exemplified herein (i.e., SEQ ID NO:1-8) or can be generated by the skilled artisan using well-known sequences encoding these components, e.g., GENBANK accession number NM_000193 for Shh (SEQ ID NO:10), GENBANK accession number NM_000264 for Ptc (SEQ ID NO:11), GENBANK accession number NM_005631 for Smo (SEQ ID NO:12), GENBANK accession number NM_016169 for Su(Fu) (SEQ ID NO:13), and GENBANK accession number NM_005269 for Gli1 (SEQ ID NO:14). The term primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers can be provided in double-stranded or single-stranded form. Probes are defined differently, although they can act as primers. Probes, while perhaps capable of priming, are designed for hybridizing to the target DNA or RNA and need not be used in an amplification process. In particular embodiments, the probes or primers are labeled with, for example, radioactive species ($^{32}$P, $^{14}$C, $^{35}$S, $^{3}$H, or other label) or a fluorophore (rhodamine, fluorescein). Depending on the application, the probes or primers can be used cold, i.e., unlabeled, and the RNA or cDNA molecules are labeled.

Various RT-PCR methodologies can be employed to evaluate the level of RNA transcript present in a sample. As clinical samples are of variable quantity and quality a relative quantitative RT-PCR reaction can be performed with an internal standard. The internal standard can be an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other assays can be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various samples is carefully normalized for equal concentrations of amplifiable cDNAs. This consideration is important since the assay measures absolute mRNA abundance. Absolute mRNA abundance can be used as a measure of differential gene expression in normalized samples. While empirical determination of the linear range of the amplification curve and normalization of cDNA preparations are tedious and time consuming processes, the resulting RT-PCR assays are generally superior to those derived from the relative quantitative RT-PCR assay with an internal standard.

Specifically contemplated by the present invention are chip-based DNA technologies. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Depending on the format, detection can be performed by visual means (e.g., ethidium bromide staining of a gel). Alternatively, detection can involve indirect identification of the product via chemiluminescence, radiolabel or fluorescent label or even via a system using electrical or thermal impulse signals (Bellus (1994) *J. Macromol. Sci. Pure Appl. Chem.* $A$311:1355-1376).

In an alternative embodiment, protein levels for one or more components of the Hedgehog pathway are detected in a NSCLC sample. In general, the detection of protein is carried out by immunoassays using antibodies which specifically bind to the Hedgehog pathway protein component of interest. Antibodies employed herein can be either polyclonal or monoclonal. Moreover, such antibodies can be natural or partially or wholly synthetically produced. All fragments or derivatives thereof which maintain the ability to specifically bind to the desired protein are also included. The antibodies can be a member of any immunoglobulin class, including any of the human classes: IgG, IgM, IgA, IgD, and IgE.

Antibody fragments can be any derivative of an antibody which is less than full-length. In general, an antibody fragment retains at least a significant portion of the full-length antibody's specific binding ability. Examples of antibody fragments include, but are not limited to, Fab, Fab', F(ab')$_2$, scFv, Fv, diabody, or Fd fragments. The antibody fragment can be produced by any means. For instance, the antibody fragment can be enzymatically or chemically produced by fragmentation of an intact antibody or it can be recombinantly produced from a gene encoding the partial antibody sequence. The antibody fragment can optionally be a single-chain antibody fragment. Alternatively, the fragment can be multiple chains which are linked together, for instance, by disulfide linkages. The fragment can also optionally be a multi-molecular complex. A functional antibody fragment typically contains at least about 50 amino acids and more typically contains at least about 200 amino acids.

An antibody for use in the methods of the present invention can be generated using classical cloning and cell fusion techniques. For example, the antigen of interest is typically administered (e.g., intraperitoneal injection) to wild-type or inbred mice (e.g., BALB/c) or transgenic mice which produce desired antibodies, or rats, rabbits or other animal species which can produce native or human antibodies. The antigen can be administered alone, or mixed with adjuvant, or expressed from a vector (VEE replicon vector), or as DNA, or as a fusion protein to induce an immune response. Fusion proteins contain the peptide against which an immune response is desired coupled to carrier proteins, such as histidine tag (his), mouse IgG2a Fc domain, β-galactosidase, glutathione S-transferase, keyhole limpet hemocyanin (KLH), or bovine serum albumin, to name a few. In these cases, the peptides serve as haptens with the carrier proteins. After the animal is boosted, for example, two or more times, the spleen is removed and splenocytes are extracted and fused with myeloma cells using the well-known processes (Kohler and Milstein (1975) *Nature* 256:495-497; Harlow and Lane (1988) Antibodies: A Laboratory Manual, Cold Spring Harbor Laboratory, New York). The resulting hybrid cells are then cloned in the conventional manner, e.g., using limiting dilution, and the resulting clones, which produce the desired monoclonal antibodies, are cultured.

Alternatively, antibodies which specifically bind a component of the Hedgehog pathway are produced by a phage display method. Methods of producing phage display antibodies are well-known in the art (e.g., Huse, et al. (1989) *Science* 246(4935):1275-81).

Selection of antigen-specific antibodies is based on binding affinity and can be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which can be performed in vitro, in vivo or in situ. Such standard techniques are well-known to those of skill in the art (see, e.g., Methods in Immunodiagnosis, 2nd Edition, Rose and Bigazzi, eds. John Wiley & Sons, 1980; Campbell et al., Methods and Immunology, W. A. Benjamin, Inc., 1964; and Oellerich, M. (1984) *J. Clin. Chem. Clin. Biochem.* 22:895-904). Antagonistic Hedgehog pathway antibodies can also be produced and selected using these methods.

Antibodies can be used in diagnostic, prognostic, or predictive methods to detect and/or quantitate the level or presence or absence of components of the Hedgehog pathway in healthy and diseased tissues by employing techniques such as ELISA, western blotting, or immunohistochemistry. Immunoassays are well-known in the art (see, for example, Harlow and Lane (1999) Using Antibodies: A Laboratory Manual, Cold Spring Harbor Laboratory Press, Cold Spring Harbor, N.Y.) and include antibody capture assays, antigen capture assays, and two-antibody sandwich assays.

Immunoassays typically rely on labeled antigens, antibodies, or secondary reagents for detection. These proteins can be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which can be employed in accordance with the present invention. The binding of these labels to antibodies or fragments thereof can be accomplished using standard techniques (e.g., Kennedy, et al. (1976) *Clin. Chim. Acta* 70:1-31; Schurs, et al. (1977) *Clin. Chim Acta* 81:1-40) and methods of detecting these labels are also well-known to the skilled artisan.

After detecting the level, presence or absence of the Hedgehog pathway component transcript or protein in a sample, the results observed for a given subject sample can be compared with a normal lung tissue from the subject or a control sample. When the comparison is conducted with a normal lung tissue sample, elevated levels of Hedgehog pathway component mRNA or protein is indicative of NSCLC in the subject from whom the sample was obtained. When a control sample from one or more subjects known to have NSCLC is employed for comparison, the level of Hedgehog pathway component mRNA or protein can be evaluated based upon there being comparable levels between the subject sample and the control sample. A control sample can also be generated from a statistically significant reference group of subjects that have NSCLC to provide diagnostic, prognostic, or predictive information pertaining the subject from whom the sample was obtained.

It is contemplated that the diagnostic method of the invention can be used alone or in combination with other well-known diagnostic or staging methods for NSCLC, e.g., chest x-rays or CAT scans. Moreover, the diagnostic method of the instant invention can be used in combination with other biomarkers for NSCLC. Such biomarkers have been identified herein by taking advantage of the gene expression profile data generated for the NCI-60 cell lines at the DTP.

The Hedgehog pathway components are also contemplated as being useful as predictors of NSCLC tumor stage and aggressiveness. For example, hyperactivated Hedgehog signaling has been correlated with increased aggressiveness of various prostate cancer cell lines and may correlate with NSCLC aggressiveness as well.

Having demonstrated that Hedgehog pathway antagonist efficacy is correlated with expression level of selected biomarkers such as Gli1 and the biomarkers listed in Table 5, the present invention is also a method for determining sensitivity of a cancer patient to treatment with antagonists of the Hedgehog pathway. Such antagonists include any small molecule, antibody, or nucleic acid-based agent which decreases the expression or activity of a component of the Hedgehog pathway. Examples of Hedgehog pathway antagonists include, but are not limited, cyclopamine, SANT1-4, Cur61414, and the like, as well as compounds listed in Table 2, and derivatives and analogs thereof (see, e.g., Table 4). This method of the present invention involves obtaining a lung tumor sample (e.g. a biopsy sample) from a patient having a cancer in which tumor cell proliferation is dependent upon Hedgehog pathway signaling (e.g., breast cancer, prostate cancer, ovarian cancer, colon cancer, SCLC, NSCLC, or pancreatic cancer); detecting in the tumor sample the level of mRNA or protein of a selected biomarker associated with sensitivity of a tumor cell to a Hedgehog pathway antagonist; and comparing the detected level to a control. A selected biomarker associated with sensitivity of a tumor cell to a Hedgehog pathway antagonist is intended to include Gli1 and the biomarkers listed in Table 6. Depending on the selected biomarker being detected, a control can vary. To illustrate, overexpression of Gli1 in the tumor sample as compared to expression of Gli1 in a control sample such as a Low-Gli tumor cell or cell line, or comparable expression of Gli1 in the tumor sample as compared to a control sample such as a High-Gli tumor cell or cell line (e.g., A549) indicates that the subject NSCLC tumor from which the sample was obtained will not be sensitive to treatment with a Hedgehog pathway antagonist i.e., the patient will not positively respond to treatment. Comparable expression of Gli1 in the tumor sample as compared to expression of Gli1 in a control sample such as a Low-Gli tumor cell or cell line, or elevated expression of Gli1 in the tumor sample as compared to a control sample such as a No-Gli tumor cell or cell line indicates that the tumor from which the sample was obtained will be sensitive to treatment with a Hedgehog pathway antagonist, i.e., the patient will positively respond to treatment and tumor size and/or number will decrease. When the biomarker being detected is selected from a biomarker listed in Table 6, differential expression of the biomarker in the tumor sample as compared to expression of the biomarker in a control sample such as a cyclopamine-insensitive tumor cell or cell line, indicates that the tumor from which the sample was obtained will be sensitive to treatment with a Hedgehog pathway antagonist. Conversely, comparable expression of a biomarker listed in Table 6 in the tumor sample as compared to expression of the biomarker in a control sample such as cyclopamine-insensitive tumor cell or cell line, indicates that the tumor from which the sample was obtained will be insensitive to treatment with a Hedgehog pathway antagonist.

As it has now been determined that resistance to Hedgehog pathway antagonists is due to overexpression of Gli1, the present invention is also a method for treating NSCLC in a patient with tumor cells that are resistant to Hedgehog pathway antagonists. Treatment involves administering to a patient with NSCLC tumor cells that are resistant to Hedgehog pathway antagonists an inhibitor of Gli1 in combination with a Hedgehog pathway antagonist so that the NSCLC is treated in the patient. The inhibitor of Gli1 is administered in an amount that effectively reduces the level or activity of Gli1 by at least 50%, 60%, 70%, 80%, 90%, 95%, 99% or 100%. In a particular embodiment, an effective amount of a Gli1 inhibitor is administered to reduce the level or activity of Gli1 by at least 90%. Effective reduction of the level or activity of Gli1 and co-administration of a Hedgehog pathway antagonist has the desired outcome reducing at least one sign or symptom of NSCLC. It is contemplated that Gli1 overexpression may also be involved in resistance of other cancer types to Hedgehog pathway antagonists and treatment of such cancers with a Gli1 inhibitor may be useful in overcoming this resistance as well.

Gli1 expression can be inhibited by introducing into or generating within a cell (i.e., transgenic expression) an siRNA or siRNA-like molecule corresponding to a Gli1-encoding nucleic acid (e.g., GENBANK Accession No. NM_005269; SEQ ID NO:14) or fragment thereof. An siRNA-like molecule refers to a nucleic acid molecule similar to an siRNA (e.g., in size and structure) and capable of eliciting siRNA activity, i.e., to effect the RNAi-mediated inhibition of expression. In various embodiments, such a method can entail the direct administration of the siRNA or siRNA-like molecule into a cell, or use of the vector-based methods. In one embodiment, the siRNA or siRNA-like molecule is less than about 30 nucleotides in length. In a further embodiment, the siRNA or siRNA-like molecule is about 21-23 nucleotides in length. In another embodiment, an siRNA or siRNA-like molecule is a 19-21 bp duplex portion, each strand having a two nucleotide 3' overhang. In particular embodiments, the siRNA or siRNA-like molecule is substantially identical to a Gli1-encoding nucleic acid or a fragment or variant (or a fragment of a variant) thereof. A particularly suitable Gli1 siRNA molecule is disclosed herein as SEQ ID NO:9. Kits for production of dsRNA for use in RNAi are available commercially, e.g., from New England Biolabs, Inc. and Ambion Inc. (Austin, Tex.). Methods of transfection of dsRNA or plasmids engineered to make dsRNA are routine in the art.

Silencing effects similar to those produced by RNAi have been reported in mammalian cells with transfection of a mRNA-cDNA hybrid construct (Lin, et al. (2001) *Biochem. Biophys. Res. Commun.* 281:639-44), providing yet another strategy for silencing a coding sequence of interest.

In a further embodiment, the Gli1 inhibitor can be a ribozyme. Ribozyme catalysis has primarily been observed as part of sequence-specific cleavage/ligation reactions involving nucleic acids (Joyce (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon, et al. (1991) *Proc. Natl. Acad. Sci. USA* 88:10591; Sarver, et al. (1990) *Science* 247:1222; Sioud, et al. (1992) *J. Mol. Biol.* 223:831).

Therefore, in particular embodiments, the invention provides antisense molecules, siRNA or siRNA-like molecules, and ribozymes for exogenous administration to effect the degradation or inhibition of the translation of Gli1 mRNA so that NSCLC tumor cells become sensitized to Hedgehog pathway antagonists.

In yet a further embodiment, a Gli1 inhibitor of the invention can be an antibody or antibody fragment. The antibody or antibody fragment can bind to Gli1 resulting in modulation of Gli1 activity (e.g., as an antagonist). Of particular interest are antagonistic antibodies which bind to and inhibit the activity of Gli1. Methods for generating suitable antibodies and methods for screening for antagonistic activity (e.g., via cell proliferation assays) are disclosed herein.

Peptide ligands or small molecule inhibitors which disrupt or block the activity of Gli1 are further contemplated as exemplary inhibitors of Gli1 activity. These agents can be identified from crystallographic analysis of Gli1 or by screening assays to identify such inhibitors. High throughput, small molecule screening assays are well-known in the art and can be cell-based or in vitro assays with purified protein.

Desirably, the Gli1 inhibitors are administered prior to or concurrently with the Hedgehog pathway antagonists. Further, the Gli1 inhibitor and Hedgehog pathway antagonist can be formulated together or separately with a pharmaceutically acceptable carrier for administration and treatment of NSCLC.

By comparing the SANT1 fingerprint generated on the NCI-60 panel of cancer cell lines with the fingerprint generated by other compounds screened against the NCI-60 panel, a plurality of compounds have now been identified which can be used to modulate the activity of the Hedgehog signaling pathway to decrease tumor cell proliferation and prevent or treat a cancer in which tumor cell proliferation is dependent upon Hedgehog pathway signaling (e.g., breast cancer, prostate cancer, ovarian cancer, colon cancer, SCLC, NSCLC, or pancreatic cancer).

Tumor cell proliferation is decreased by contacting a tumor cell, which is dependent upon the Hedgehog pathway for proliferation, with an effective amount of Compound 1-10, or a derivative or analog thereof. In particular embodiments, tumor cell proliferation is decreased by at least 50%, 60%, 70%, 80%, 90%, 95%, 99% or 100% as compared to a tumor cell which has not been contacted with a compound of the instant invention. In vitro cell proliferation measurements can be determined by counting cells before and after contacting the tumor cells with a compound of the invention and comparing the number of cells present after addition of the compound to tumor cells not contacted with the compound. Decreasing tumor cell proliferation can be used in the prevention or treatment of cancer or for determining what other factors (e.g., genes) are associated with cancer proliferation.

Prevention or treatment of a cancer in which tumor cell proliferation is dependent upon Hedgehog pathway signaling involves administering an effective amount of a compound of the instant invention so that at least one sign or symptoms associated with the cancer is reduced. General signs or symptoms that can be monitored to ascertain treatment effectiveness, include but are not limited to, tumor size, pain perception, or weakness.

Exemplary compounds for decreasing tumor cell proliferation and preventing or treating a cancer include Compounds 1-10 disclosed in Table 2, and derivatives and analogs thereof (see, e.g., Table 4) which have a structure similar to that of Compounds 1-10 and retain the same biological activity. For example, the halogen group of, e.g., Compounds 2, 3 and 5 can be substituted with another halogen group such as a fluoro, chloro, bromo or iodo group. Enantiomers, isomers, and tautomers of Compounds 1-10 are also expressly encompassed by the instant invention as are pure enantiomers or pure diastereomers or mixtures of enantiomers. Derivatives, analogs, enantiomers, isomers, and tautomers of Compounds 1-10 can be screened for activity using the tumor cell lines disclosed herein, cells transformed with Shh reporter constructs, or animal models of cancer. As will be appreciated by those of skill in the art upon reading this disclosure, additional compounds for screening can be selected randomly by one skilled in the art, based upon computational prediction, and/or based upon their containing a structure similar to that of the exemplary compounds disclosed herein. In this regard, particular embodiments of the present invention embrace derivatives of NSC668332 having the structure set forth in Formula I

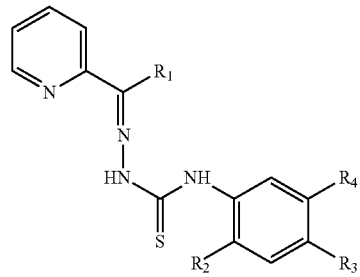

Formula I wherein $R_1$ is an $C_1$-$C_4$ alkyl, $C_6$-$C_{10}$ aryl or $C_3$-$C_8$ cycloalkyl; $R_2$ is hydrogen, halogen (e.g., Cl, F, Br, I), or $C_1$-$C_4$ alkyl; and $R_3$ and $R_4$ are independently hydrogen or $C_1$-$C_4$ alkyl. Compounds falling within the scope of Formula I have been shown to inhibit the expression Hedgehog pathway signaling and are therefore useful in decreasing tumor cell proliferation and preventing or treating a cancer in accordance with the methods disclosed herein.

For therapeutic use, the Gli1 inhibitor, Hedgehog pathway antagonist, and compounds disclosed herein, collectively referred to hereafter as "agents", are generally formulated with a pharmaceutically acceptable carrier at an appropriate dose. Such pharmaceutical compositions can be prepared by methods and contain carriers which are well known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

What is claimed is:

1. A method for treating non-small cell lung carcinoma in a patient with tumor cells that are resistant to Hedgehog pathway antagonists comprising administering to a patient with non-small cell lung carcinoma tumor cells that are resistant to Hedgehog pathway antagonists, an inhibitor of Gli1 in combination with Compound 6 thereby treating the non-small cell lung carcinoma in the patient.

* * * * *

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
ggagtctctg cactacgag                                                    19

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
gtcgctgtag agcagccg                                                     18

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
agtagctatg gcgagccct                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
taggagcctc ctggagatgt                                                   20
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
cttcgctctg gagcagattt                                                   20

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
caggacatta gcaccttct                                                    19

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
caacctgttt gccatgtttg ga                                                22

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ctgtgtccat caggttggtg                                                   20

<210> SEQ ID NO 9
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 9
aacuccacag gcauacagga u                                                 21

<210> SEQ ID NO 10
<211> LENGTH: 1576
<212> TYPE: DNA
<213> ORGANISM: Homo sapiens

<400> SEQUENCE: 10
gcgaggcagc cagcgaggga gagagcgagc gggcgagccg gagcgaggaa gggaaagcgc       60
aagagagagc gcacacgcac acacccgccg cgcgcactcg cgcacggacc cgcacgggga      120
cagctcggaa gtcatcagtt ccatgggcga gatgctgctg ctggcgagat gtctgctgct      180
agtcctcgtc tcctcgctgc tggtatgctc gggactggcg tgcggaccgg gcaggggggtt     240 cgggaagagg aggcacccca aaaagctgac ccctttagcc tacaagcagt ttatccccaa      300
tgtggccgag aagaccctag gcgccagcgg aaggtatgaa gggaagatct ccagaaactc      360
```

| | |
|---|---|
| cgagcgattt aaggaactca cccccaatta caaccccgac atcatattta aggatgaaga | 420 |
| aaacaccgga gcggacaggc tgatgactca gaggtgtaag gacaagttga acgctttggc | 480 |
| catctcggtg atgaaccagt ggccaggagt gaaactgcgg gtgaccgagg gctgggacga | 540 |
| agatggccac cactcagagg agtctctgca ctacgagggc cgcgcagtgg acatcaccac | 600 |
| gtctgaccgc gaccgcagca agtacggcat gctggcccgc ctggcggtgg aggccggctt | 660 |
| cgactgggtg tactacgagt ccaaggcaca tatccactgc tcggtgaaag cagagaactc | 720 |
| ggtggcggcc aaatcgggag gctgcttccc gggctcggcc acggtgcacc tggagcaggg | 780 |
| cggcaccaag ctggtgaagg acctgagccc cggggaccgc gtgctggcgg cggacgacca | 840 |
| gggccggctg ctctacagcg acttcctcac tttcctggac cgcgacgacg gcgccaagaa | 900 |
| ggtcttctac gtgatcgaga gcgcgggagc gcgcgagcgc ctgctgctca ccgccgcgca | 960 |
| cctgctcttt gtggcgccgc acaacgactc ggccaccggg gagcccgagg cgtcctcggg | 1020 |
| ctcggggccg ccttccgggg gcgcactggg gcctcgggcg ctgttcgcca gccgcgtgcg | 1080 |
| cccgggccag cgcgtgtacg tggtggccga gcgtgacggg gaccgccggc tcctgcccgc | 1140 |
| cgctgtgcac agcgtgaccc taagcgagga ggccgcgggc gcctacgcgc cgctcacggc | 1200 |
| ccagggcacc attctcatca accgggtgct ggcctcgtgc tacgcggtca tcgaggagca | 1260 |
| cagctgggcg caccgggcct tcgcgcccct ccgcctggcg cacgcgctcc tggctgcact | 1320 |
| ggcgcccgcg cgcacggacc gcggcgggga cagcggcggc ggggaccgcg ggggcggcgg | 1380 |
| cggcagagta gccctaaccg ctccaggtgc tgccgacgct ccgggtgcgg gggccaccgc | 1440 |
| gggcatccac tggtactcgc agctgctcta ccaaataggc acctggctcc tggacagcga | 1500 |
| ggccctgcac ccgctgggca tggcggtcaa gtccagctga agccgggggg ccggggagg | 1560 |
| ggcgcgggag ggggcg | 1576 |

<210> SEQ ID NO 11
<211> LENGTH: 6825
<212> TYPE: DNA
<213> ORGANISM: Homo sapiens

<400> SEQUENCE: 11

| | |
|---|---|
| gcgcccgccg tgtgagcagc agcagcggct ggtctgtcaa ccggagcccg agcccgagca | 60 |
| gcctgcggcc agcagcgtcc tcgcaagccg agcgcccagg cgcgccagga gcccgcagca | 120 |
| gcggcagcag cgcgccgggc cgcccgggaa gcctccgtcc ccgcggcggc ggcggcggcg | 180 |
| gcggcaacat ggcctcggct ggtaacgccg ccgagcccca ggaccgcggc ggcggcggca | 240 |
| gcggctgtat cggtgccccg ggacggccgg ctggaggcgg gaggcgcaga cggacggggg | 300 |
| gctgcgccgc tgctgccgcg ccggaccggg actatctgca ccggcccagc tactgcgacg | 360 |
| ccgccttcgc tctggagcag atttccaagg ggaaggctac tggccggaaa gcgccgctgt | 420 |
| ggctgagagc gaagtttcag agactcttat ttaaactggg ttgttacatt caaaaaaact | 480 |
| gcggcaagtt cttggttgtg ggcctcctca tatttgggc cttcgcggtg ggattaaaag | 540 |
| cagcgaacct cgagaccaac gtggaggagc tgtgggtgga agttggagga cgagtaagtc | 600 |
| gtgaattaaa ttatactcgc cagaagattg agaagaggc tatgtttaat cctcaactca | 660 |
| tgatacagac ccctaaagaa gaaggtgcta atgtcctgac cacagaagcg ctcctacaac | 720 |
| acctggactc ggcactccag gccagccgtg tccatgtata catgtacaac aggcagtgga | 780 |
| aattggaaca tttgtgttac aaaatcagga gagcttatca cagaaacaggt tacatggatc | 840 |
| agataataga atatctttac ccttgtttga ttattacacc tttggactgc ttctgggaag | 900 |

```
gggcgaaatt acagtctggg acagcatacc tcctaggtaa acctcctttg cggtggacaa    960
acttcgaccc tttggaattc ctggaagagt taaagaaaat aaactatcaa gtggacagct   1020
gggaggaaat gctgaataag gctgaggttg gtcatggtta catggaccgc ccctgcctca   1080
atccggccga tccagactgc cccgccacag cccccaacaa aaattcaacc aaacctcttg   1140
atatggccct tgttttgaat ggtggatgtc atggcttatc agaaagtat atgcactggc    1200
aggaggagtt gattgtgggt ggcacagtca agaacagcac tggaaaactc gtcagcgccc   1260
atgccctgca gaccatgttc cagttaatga ctcccaagca aatgtacgag cacttcaagg   1320
ggtacgagta tgtctcacac atcaactgga acgaggacaa agcggcagcc atcctggagg   1380
cctggcagag gacatatgtg gaggtggttc atcagagtgt cgcacagaac tccactcaaa   1440
aggtgctttc cttcaccacc acgaccctgg acgacatcct gaaatccttc tctgacgtca   1500
gtgtcatccg cgtggccagc ggctacttac tcatgctcgc ctatgcctgt ctaaccatgc   1560
tgcgctggga ctgctccaag tcccaggtgt ccgtggggct ggctggcgtc ctgctggttg   1620
cactgtcagt ggctgcagga ctgggcctgt gctcattgat cggaatttcc tttaacgctg   1680
caacaactca ggttttgcca tttctcgctc ttggtgttgg tgtggatgat gttttcttc    1740
tggcccacgc cttcagtgaa acaggacaga ataaaagaat ccctttgag acaggaccg     1800
gggagtgcct gaagcgcaca ggagccagcg tggccctcac gtccatcagc aatgtcacag   1860
ccttcttcat ggccgcgtta atcccaattc ccgctctgcg ggcgttctcc ctccaggcag   1920
cggtagtagt ggtgttcaat tttgccatgg ttctgctcat ttttcctgca attctcagca   1980
tggatttata tcgacgcgag gacaggagac tggatatttt ctgctgtttt acaagcccct   2040
gcgtcagcag agtgattcag gttgaacctc aggcctacac cgacacacac gacaataccc   2100
gctacagccc cccacctccc tacagcagcc acagctttgc ccatgaaacg cagattacca   2160
tgcagtccac tgtccagctc cgcacggagt acgaccccca cacgcacgtg tactacacca   2220
ccgctgagcc gcgctccgag atctctgtgc agcccgtcac cgtgacacag gacaccctca   2280
gctgccagag cccagagagc accagctcca aagggacct gctctcccag ttctccgact   2340
ccagcctcca ctgcctcgag ccccctgta cgaagtggac actctcatct tttgctgaga   2400
agcactatgc tccttttcctc ttgaaaccaa aagccaaggt agtggtgatc ttcctttttc   2460
tgggcttgct gggggtcagc ctttatggca ccacccgagt gagagacggg ctggaccta   2520
cggacattgt acctcgggaa accagagaat atgactttat tgctgcacaa ttcaaatact   2580
tttcttctta caacatgtat atagtcaccc agaaaagcaga ctaccgaat atccagcact   2640
tactttacga cctacacagg agtttcagta acgtgaagta tgtcatgttg gaagaaaaca   2700
aacagcttcc caaaatgtgg ctgcactact tcagagactg gcttcaggga cttcaggatg   2760
catttgacag tgactgggaa accgggaaaa tcatgccaaa caattacaag aatggatcag   2820
acgatggagt ccttgcctac aaactcctgg tgcaaaccgg cagccgcgat aagcccatcg   2880
acatcagcca gttgactaaa cagcgtctgg tggatgcaga tggcatcatt aatcccagcg   2940
ctttctacat ctacctgacg gcttgggtca gcaacgaccc cgtcgcgtat gctgcctccc   3000
aggccaacat ccggccacac cgaccagaat gggtccacga caaagccgac tacatgcctg   3060
aaacaaggct gagaatcccg gcagcagagc ccatcgagta tgcccagttc ccttttctacc   3120
tcaacggctt gcgggacacc tcagactttg tggaggcaat tgaaaaagta aggaccatct   3180
gcagcaacta tacgagcctg gggctgtcca gttaccccaa cggctacccc ttcctcttct   3240
gggagcagta catcggcctc cgccactggc tgctgctgtt catcagcgtg gtgttggcct   3300
```

```
gcacattcct cgtgtgcgct gtcttccttc tgaacccctg gacggccggg atcattgtga    3360
tggtcctggc gctgatgacg gtcgagctgt tcggcatgat gggcctcatc ggaatcaagc    3420
tcagtgccgt gcccgtggtc atcctgatcg cttctgttgg cataggagtg gagttcaccg    3480
ttcacgttgc tttggccttt ctgacggcca tcggcgacaa gaaccgcagg gctgtgcttg    3540
ccctggagca catgtttgca cccgtcctgg atggcgccgt gtccactctg ctgggagtgc    3600
tgatgctggc gggatctgag ttcgacttca ttgtcaggta tttctttgct gtgctggcga    3660
tcctcaccat cctcggcgtt ctcaatgggc tggttttgct tcccgtgctt ttgtcttttct    3720
ttggaccata tcctgaggtg tctccagcca acggcttgaa ccgcctgccc acccctccc    3780
ctgagccacc ccccagcgtg gtccgcttcg ccatgccgcc cggccacacg cacagcgggt    3840
ctgattcctc cgactcggag tatagttccc agacgacagt gtcaggcctc agcgaggagc    3900
ttcggcacta cgaggcccag cagggcgcgg gaggccctgc ccaccaagtg atcgtggaag    3960
ccacagaaaa ccccgtcttc gcccactcca ctgtggtcca tcccgaatcc aggcatcacc    4020
caccctcgaa cccgagacag cagccccacc tggactcagg gtccctgcct cccggacggc    4080
aaggccagca gccccgcagg gaccccccca gagaaggctt gtggccaccc ctctacagac    4140
cgcgcagaga cgcttttgaa atttctactg aagggcattc tggccctagc aatagggccc    4200
gctgggggccc tcgcggggcc cgttctcaca accctcggaa cccagcgtcc actgccatgg    4260
gcagctccgt gcccggctac tgccagccca tcaccactgt gacggcttct gcctccgtga    4320
ctgtcgccgt gcaccgccg cctgtccctg ggcctgggcg gaaccccga ggggactct      4380
gcccaggcta ccctgagact gaccacgcc tgtttgagga cccccacgtg cctttccacg    4440
tccggtgtga gaggagggat tcgaaggtgg aagtcattga gctgcaggac gtggaatgcg    4500
aggagaggcc ccggggaagc agctccaact gagggtgatt aaaatctgaa gcaaagaggc    4560
caaagattgg aaaccccca ccccacctc tttccagaac tgcttgaaga gaactggttg    4620
gagttatgga aaagatgccc tgtgccagga cagcagttca ttgttactgt aaccgattgt    4680
attattttgt taaatatttc tataaatatt taagagatgt acacatgtgt aatataggaa    4740
ggaaggatgt aaagtggtat gatctggggc ttctccactc ctgccccaga gtgtggaggc    4800
cacagtgggg cctctccgta tttgtgcatt gggctccgtg ccacaaccaa gcttcattag    4860
tcttaaattt cagcatatgt tgctgctgct taaatattgt ataatttact tgtataattc    4920
tatgcaaata ttgcttatgt aataggatta ttttgtaaag gtttctgttt aaaatatttt    4980
aaatttgcat atcacaaccc tgtggtagta tgaaatgtta ctgttaactt tcaaacacgc    5040
tatgcgtgat aattttttg tttaatgagc agatatgaag aaagcacgtt aatcctggtg    5100
gcttctctag gtgtcgttgt gtgcggtcct cttgttggc tgtgcgtgtg aacacgtgtg    5160
tgagttcacc atgtactgta ctgtgatttt tttttgtct tgttttgttt ctctacactg    5220
tctgtaacct gtagtaggct ctgacctagt caggctggaa gcgtcaggat atctttctt    5280
cgtgctggtg agggctggcc ctaaacatcc acctaatcct ttcaaatcag cccggcaaaa    5340
gctagactct cctcgtgtct acggcatctc ttatgatcat tggctgccat ccaggaccc    5400
aatttgtgct tcaggggat aatctccttc tctcggatca ttgtgatgga tgctggaacc    5460
tcagggtatg gagctcacat cagttcatca tggtgggtgt tagagaattc ggtgacatgc    5520
ctagtgctga gccttggctg ggccatgaga gtctgtatac tctaaaaagc atgcagcatg    5580
gtgcccctct tctgaccaac acacacacga cccctccccc aacacccca aattcaagag    5640
tggatgtggc cctgtcacag gtagaaaaac ctatttagtt aattcttcct tggcccacag    5700
```

```
tctcccagaa atgatgtttt gagtccctat agtttaaact ccctctctta aatggagcag    5760
ctggttgagg ctttctagat ctgtttgcat cttctttaaa actaagtggt gagcatgcat    5820
tgtggtgtag aggcaggcat tatgtaggat aagagctccg gggggattct tcatgcacca    5880
gtgtttaggg tacgtgcttc ctaagtaaat ccaaacattg tctccatcct ccccgtcatt    5940
agtgctcttt caatgtgatg tgggaaagca ggaggatgga cacacccccac tgaaagatgt    6000 aggcaggggc aggtctctca accaggcata tttttaaaag ttgcttctgt actggttctc    6060
ttcttttgct ctgaggtgtg ggctccctca tctcgtaacc agagaccagc acatgtcagg    6120
gaagcaccca gtgtcggctc cccatccaaa tccacaccag caccttgtta cagacaagaa    6180
gtcagaggaa agggcggggt ccctgcaggg ctgaagccta agctactgtg aggcgctcac    6240
gagtggcagc tcctgttact cccttttaaa ttacctggga aatcttaaca gaaaggtaat    6300
gggcccccag aaatacccac agcatagtga cctcagaccc tgatactcac cacaaaactt    6360
ttaagatgct gattgggagc cgcttgtggc tgctgggtgt gtgtgtgtgt gtgtgcgtgc    6420
gtgcgtgtgt gtgtgtctct gctggggacc ctggccaccc cctgctgct gtcttggtgc    6480 ctgtcaccca catggtctgc catcctaaca cccagctctg ctcagaaaac gtcctgcgtg    6540
gaggagggat gatgcagaat tctgaagtcg acttccctct ggctcctggc gtgccctcgc    6600
tcccttcctg agcccagctc gtgttgcgcc ggaggctgcg cggcccctga tttctgcatg    6660
gtgtagaact ttctccaata gtcacattgg caaagggaga actggggtgg gcggggggtg    6720
gggctggcag ggaattagaa tttctctctc tcttttaata gttttatttt gtctgtcctg    6780
tttgttcatt tggatgtttt aattttttaaa aaaaaaaaaa aaaaa                  6825

<210> SEQ ID NO 12
<211> LENGTH: 3772
<212> TYPE: DNA
<213> ORGANISM: Homo sapiens

<400> SEQUENCE: 12
gggctgaaga caacttggat tgcgaggcta gggcttgggg agtcgtgcat cccgttccgg      60
gcctccgcag cccaacatgg gccccgggtt ccaaagtttg cgaagtttgg cgccgagggg     120
ccggggcgcg cggagcgtcc ggggggggccc gggcccggat tctctgggcg cacaggtcgc     180
ctgagccgcc tccgcggccg ccgaggtcgt gcgtgtggcc ggggggctcc gaggagcagg     240
cgggggcgcc ggggcttttg ctgagttggc ggggttggcc atggccgctg cccgcccagc     300 gcggggccg gagctcccgc tcctgggct gctgctgctg ctgctgctgg ggacccggg        360 ccgggggcg gcctcgagcg ggaacgcgac cgggcctggg cctcggagcg cggcgggag       420 cgcgaggagg agcgcggcgg tgactggccc tccgccgccg ctgagccact gcggccgggc    480
tgccccctgc gagccgctgc gctacaacgt gtgcctgggc tcggtgctgc cctacggggc    540
cacctccaca ctgctggccg gagactcgga ctcccaggag gaagcgcacg gcaagctcgt    600
gctctggtcg ggcctccgga atgccccccg ctgctgggca gtgatccagc ccctgctgtg    660
tgccgtatac atgcccaagt gtgagaatga ccggtggag ctgccagcc gtaccctctg      720 ccaggccacc cgaggcccct gtgccatcgt ggagagggag cggggctggc ctgacttcct    780
gcgctgcact cctgaccgct tccctgaagg ctgcacgaat gaggtgcaga acatcaagtt    840
caacagttca ggccagtgcg aagtgccctt ggttcggaca gacaaccccca agagctggta    900 cgaggacgtg gagggctgcg gcatccagtg ccagaaccg ctcttcacag aggctgagca    960
ccaggacatg cacagctaca tcgcggcctt cggggccgtc acgggcctct gcacgctctt   1020
```

```
caccctggcc acattcgtgg ctgactggcg gaactcgaat cgctaccctg ctgttattct    1080
cttctacgtc aatgcgtgct tctttgtggg cagcattggc tggctggccc agttcatgga    1140
tggtgcccgc cgagagatcg tctgccgtgc agatggcacc atgaggcttg gggagcccac    1200
ctccaatgag actctgtcct gcgtcatcat ctttgtcatc gtgtactacg ccctgatggc    1260
tggtgtggtt tggtttgtgg tcctcaccta tgcctggcac acttccttca aagccctggg    1320
caccacctac cagcctctct cgggcaagac ctcctacttc cacctgctca cctggtcact    1380
cccctttgtc ctcactgtgg caatccttgc tgtggcgcag gtggatgggg actctgtgag    1440
tggcatttgt tttgtgggct acaagaacta ccgataccgt gcgggcttcg tgctggcccc    1500
aatcggcctg gtgctcatcg tgggaggcta cttcctcatc cgaggagtca tgactctgtt    1560
ctccatcaag agcaaccacc ccgggctgct gagtgagaag gctgccagca agatcaacga    1620
gaccatgctg cgcctgggca ttttttggctt cctggccttt ggctttgtgc tcattacctt    1680
cagctgccac ttctacgact tcttcaacca ggctgagtgg gagcgcagct tccgggacta    1740
tgtgctatgt caggccaatg tgaccatcgg gctgcccacc aagcagccca tccctgactg    1800
tgagatcaag aatcgcccga gccttctggt ggagaagatc aacctgtttg ccatgtttgg    1860
aactggcatc gccatgagca cctgggtctg gaccaaggcc acgctgctca tctggaggcg    1920
tacctggtgc aggttgactg ggcagagtga cgatgagcca aagcggatca agaagagcaa    1980
gatgattgcc aaggccttct ctaagcggca cgagctcctg cagaacccag gccaggagct    2040
gtccttcagc atgcacactg tgtcccacga cggggcccgtg gcgggcttgg cctttgacct    2100
caatgagccc tcagctgatg tctcctctgc ctgggcccag catgtcacca agatggtggc    2160
tcggagagga gccatactgc cccaggatat ttctgtcacc cctgtggcaa ctccagtgcc    2220
cccagaggaa caagccaacc tgtggctggt tgaggcagag atctccccag agctgcagaa    2280
gcgcctgggc cggaagaaga agaggaggaa gaggaagaag gaggtgtgcc cgctggcgcc    2340
gccccctgag cttcaccccc ctgccctgc ccccagtacc attcctcgac tgcctcagct    2400
gccccggcag aaatgcctgg tggctgcagg tgcctgggga ctggggact cttgccgaca    2460
gggagcgtgg accctggtct ccaacccatt ctgcccagag cccagtcccc ctcaggatcc    2520
atttctgccc agtgcaccgg ccccgtggc atgggctcat ggccgccgac agggcctggg    2580
gcctattcac tcccgcacca acctgatgga cacagaactc atggatgcag actcggactt    2640
ctgagcctgc agagcaggac ctgggacagg aaagagagga accaatacct tcaaggctct    2700
tcttcctcac cgagcatgct tccctaggat cccgtcttcc agagaacctg tgggctgact    2760
gccctccgaa gagagttctg gatgtctggc tcaaagcagc aggactgtgg gaaagagcct    2820
aacatctcca tggggaggcc tcaccccagg acagggccc tggagctcag ggtccttgtt    2880
tctgccctgc cagctgcagc ctggttggca gcatctgctc catcggggca ggggtatgc    2940
agagcttgtg gtggggcagg aacggtggag gcagaggtga cagttcccag agtgggcttt    3000
ggtggccagg gaggcagcct agcctatgtc tggcagatga gggctggctg ccgttttctg    3060
ggctgatggg tgcccttcc tggcagtctc agtccaaaag tgttgactgt gtcattagtc    3120
ctttgtctaa gtagggccag gcaccgtat tcctctccca ggtgtttgtg gggctggaag    3180
gacctgctcc cacaggggcc atgtcctctc ttaataggtg gcactacccc aaacccatct    3240
tttgttctcc tatatcctcc ttctcctgtt ccatttcagt tcagtttcag cggtgccaac    3300
ctctttgcgt ttcctttttg ttgatgagga cccagagctg ctgcacacac tcacctctaa    3360
cccctctccc tcgctgctgg gccccatctc cacaggagag actggttcgg ctctagggcc    3420
```

-continued

| | |
|---|---|
| tcagtctgga gtgggatagg agcagtgagt gacaaagcct ctgaaagatg catcatctct | 3480 |
| tcctcacacc catttagtgg gggatgggtc ctctagactt gagggggctac cctgggaagc | 3540 |
| tgccgtagct tcagccaggc aagaaagctt ccttcaacct gcatagccgg tgggtgagga | 3600 |
| gattcccacc ttccatagcc tccaaacatg ttcccaaggc cccactttca agaatcagac | 3660 |
| agcaggaagc catagatgct ggctgggttc caggttatgg ggagaagaaa tacagtcaat | 3720 |
| aaaaggtttt tgtataaaaa aaaaaaaaaa aaaaaaaaaa aaaaaaaaaa aa | 3772 |

<210> SEQ ID NO 13
<211> LENGTH: 4898
<212> TYPE: DNA
<213> ORGANISM: Homo sapiens

<400> SEQUENCE: 13

| | |
|---|---|
| cgccgtgcgc aggcgcggag ctagacctcg ctgcagcccc catcgcctcg ggagtctca | 60 |
| cccaccgagt ccgcccgctg gcccgtcagt gctctcccg tcgtttgccc tctccagttc | 120 |
| ccccagtgcc tgccctacgc accccgatgg cggagctgcg gcctagcggc gcccccggcc | 180 |
| ccaccgcgcc cccggcccct ggcccgactg ccccccccggc cttcgcttcg ctctttcccc | 240 |
| cgggactgca cgccatctac ggagagtgcc gccgccttta ccctgaccag ccgaacccgc | 300 |
| tccaggttac cgctatcgtc aagtactggt tgggtggccc agaccccttg gactatgtta | 360 |
| gcatgtacag gaatgtgggg agcccttctg ctaacatccc cgagcactgg cactacatca | 420 |
| gcttcggcct gagtgatctc tatggtgaca acagagtcca tgagtttaca ggaacagatg | 480 |
| gacctagtgg tttttggcttt gagttgacct ttcgtctgaa gagagaaact ggggagtctg | 540 |
| ccccaccaac atggcccgca gagttaatgc agggcttggc acgatacgtg ttccagtcag | 600 |
| agaacacctt ctgcagtggg gaccatgtgt cctggcacag ccctttggat aacagtgagt | 660 |
| caagaattca gcacatgctg ctgacagagg acccacagat gcagcccgtg cagacaccct | 720 |
| ttgggggtagt taccttcctc cagatcgttg gtgtctgcac tgaagagcta cactcagccc | 780 |
| agcagtggaa cgggcagggc atcctggagc tgctgcggac agtgcctatt gctggcggcc | 840 |
| cctggctgat aactgacatg cggaggggag agaccatatt tgagatcgat ccacacctgc | 900 |
| aagagagagt tgacaaaggc atcgagacag atggctccaa cctgagtggt gtcagtgcca | 960 |
| agtgtgcctg ggatgacctg agccggcccc ccgaggatga cgaggacagc cggagcatct | 1020 |
| gcatcggcac acagccccgg cgactctctg gcaaagacac agagcagatc cgggagaccc | 1080 |
| tgaggagagg actcgagatc aacagcaaac ctgtccttcc accaatcaac cctcagcggc | 1140 |
| agaatggcct cgcccacgac cgggcccccga gccgcaaaga cagcctggaa agtgacagct | 1200 |
| ccacggccat cattccccat gagctgattg cacgcggca gcttgagagc gtacatctga | 1260 |
| aattcaacca ggagtccgga gccctcattc ctctctgcct aaggggcagg ctcctgcatg | 1320 |
| gacggcactt tacatataaa agtatcacag gtgacatggc catcacgttt gtctccacgg | 1380 |
| gagtggaagg cgcctttgcc actgaggagc atccttacgc ggctcatgga ccctggttac | 1440 |
| aaattctgtt gaccgaagag tttgtagaga aatgttgga ggatttagaa gatttgactt | 1500 |
| ctccagagga attcaaactt cccaaagagt acagctggcc tgaaaagaag ctgaaggtct | 1560 |
| ccatcctgcc tgacgtggtg ttcgacagtc cgctacacta gcctgggctg ggccctgcag | 1620 |
| gggccagcag ggagcccagc tgctccccag tgacttccag tgtaacagtt gtgtcaacga | 1680 |
| gatctccaca aataaaagga caagtgtgag gaagactgcg cagtgccacc ccgcagccca | 1740 |
| gtggggtgcc atgcacaggc cacaggccct ccacctcacc tccagctcag gggccgcacc | 1800 |

```
ccgccgctgg ctaagccttg tgacccatca ggccagtgag tgggcaaatg cggaccctcc    1860
ctgcctgcag cctgcacaga ttctggtttg aggtttgact ctggaccctg gctgtgcccc    1920
taggtggaga cagccctctt tctcacctac ccctgccgc acagcccagc aggagggagg     1980
cggacagcca gatgcagagc gagtggatgc acttcccagc tcatctctgg aagcctttgc    2040
tactcaagct cctctggccg cggaacaatt cctctgatca tgtttggttt tcttcttcct    2100
tattttattt tgtagaaacc gggtggtatt ttattgctct gcaaagatgt ccagaagcca    2160
tgtatataat gttttttaaa cagaacttca ttccccgttg aactttcgca ttctctgaca    2220
gaggcctagg gctgtatctc tccctgggct gccaccagag aaggtgcttg gtgttcgcct    2280
gccagcccag agccctggag gagccggctg cacagagagg cttttcttcc cagctgggcc    2340
tgatggagcc cggggcaggg ggagagtaga gacactccct tgtgcagctt tgagcctagt    2400
ttagctgggg ccagggaggg gtgctactgt tttccaagtg aatgggtctc aaagacttgg    2460 tgacccccagc ctcatcttct aggccttttc catccaacca ggcctacctg ggagagggtg    2520
aggttcagca catcacacac catccccact gtcattcagg gcctgggtct ccagctctgt    2580
aaccagtcct gtcccatttc ctcagtccct gggcctccca gccttcaggc tgtagggctg    2640
ccttactaaa attgaaaaat ccacctctta acatctcttt cactttggtt ttgctaacac    2700
tgctctctgc tgccctccca tcctccctgt atccattcat gccctatctt tcattctcca    2760
ctcctaatcc ctctcctttc tggcatcctg gcctctcgtg gtcctcagcc cctcaccccc    2820
agtactgcag atctcacagt ttgccttcca gaagccagcc tatctctagc ccatggtttt    2880
ggagttcctc tcgggttatc tcccacgcct gacctggaac cagcaagccc ctttcctgcc    2940
ttcttacccc caactctagg gatgggactg ttacaatact tcaagatcac tctttacacc    3000
tcttcaaagc aaagtcatga caatgcaggg ctcctcattg ctcccatctg cctctgctgc    3060
acacacaggc accagcaggg atgccacagg agtgcccaca gggtgcagga ctccactgat    3120
gagagatcca gccaaagagc tgcccccagg ggtatgaggg caccagctgg gttctccagg    3180
gagcaggagt tggacctcca tggagccact aggcctggcc tcctctacac atccccaggg    3240
ctatctggtt aattccatca agctcagagt taaaaggcat atcagcctgg agtatttggg    3300
agagactggc tgcagatccc cgccagccaa gatgcaagcc actcgggacc tgatgtcggc    3360
agctgtgcct ctactgccct gaggacttac cagagggagc cctactggcc ttcccccacc    3420
acagcagccc tgcctgtgaa gctcttgttt ctgacatttc acaggcagag aggtgccatc    3480
agttcgcctc cattccttgc caccatgacc agcctctccc tgaactctct cttgctcggg    3540
acctgcctga gggctcccctg ctgcagttcg ccgtacttcc atctgctggg tgcctccatc    3600
gttggttggg tggggatggg gcattttctg agctaagctt tgtcattagt ttgtgaagca    3660
cctggtcagc aacctgcccc agacctggag ggtctttgtg gactgaaggt agacaccagc    3720
cagcatggtg gccctgttct gggggagcag ggtaaggcag gaggaagtgg gtgagctccg    3780
agatgatgag cacatgaagc ctgtggcccc ttcgtacctg caatatgtca ggagcctcac    3840
gctcacccaa gatcctgcag gggccaggct ccatctcact ggctctgagg caggacagg     3900 gtatcacaca tttctcacca ggcctccttt cctatgggca ttggtgcctc ccagaggttt    3960
cttgggctgc tggctggtga gagaggaccc ttaaagaaga tcaagccaag ctgaccttgg    4020
accctgtcca gcacagcttc tggcacagga tgcttggtga atgtaccctt tctttccctc    4080
cctgcagctc tgagggagcc cctgaccttg tagtgggtgg aggaggtaag gggcctccct    4140
ccctaaatct gcctcttctg caagctactt ggagacttgc ctagttgtac ccacccctcc    4200
```

-continued

| | |
|---|---|
| aggtccctgg tgctagagct tctgagaagg gcctttccct ttcctctttg cctgctatat | 4260 |
| aaggcaggct cctgtggctc tgctggctca gtgtgggctg caggaggact gcagactcag | 4320 |
| ctgcaattct gagggggggtt tgggaggctt gtgcgaggtc tcaggcctgt gtgggagct | 4380 |
| ggtgcctctt cctgcccgta tctttctctt ccaaggcag tgctccaagg cagggactgg | 4440 |
| agaagccaag gggagagtct aaaagggcta gagcatttt aaaaatagac acagggtctt | 4500 |
| gggactgggg tttcggattg agttgcaagc agggagaaaa cctgaaggtc ggtgcccta | 4560 |
| tggggctgac cagtagagaa tttcctttac tgtatttttg tgtctggtct tcccttctg | 4620 |
| gcttctagga catccatgcc aggtgaggtg cctgggtccc tgttacaagt caggagccct | 4680 |
| gtagggagac ccctcctttt gtacaagtac ctgaatgctg cgacaagcag attttttgtaa | 4740 |
| aattttatat tagtttttaa tgtcagtggc gactcggttc ctggggctgc agccagcctg | 4800 |
| ggacttttgt aagaattttt gggtgactca cttagatgtc gtttccttct tgcccctct | 4860 |
| tcctctctgt aatctaagtg cattaaacat ctttgcag | 4898 |

```
<210> SEQ ID NO 14
<211> LENGTH: 3600
<212> TYPE: DNA
<213> ORGANISM: Homo sapiens

<400> SEQUENCE: 14
```

| | |
|---|---|
| cccagactcc agccctggac cgcgcatccc gagcccagcg cccagacaga gtgtccccac | 60 |
| accctcctct gagacgccat gttcaactcg atgaccccac caccaatcag tagctatggc | 120 |
| gagccctgct gtctccggcc cctccccagt caggggggccc ccagtgtggg gacagaagga | 180 |
| ctgtctggcc cgcccttctg ccaccaagct aacctcatgt ccggccccca cagttatggg | 240 |
| ccagccagag agaccaacag ctgcaccgag ggcccactct tttcttctcc ccggagtgca | 300 |
| gtcaagttga ccaagaagcg ggcactgtcc atctcacctc tgtcggatgc cagcctggac | 360 |
| ctgcagacgg ttatccgcac ctcacccagc tccctcgtag ctttcatcaa ctcgcgatgc | 420 |
| acatctccag gaggctccta cggtcatctc tccattggca ccatgagccc atctctggga | 480 |
| ttcccagccc agatgaatca ccaaaaaggg ccctcgcctt cctttgggt ccagccttgt | 540 |
| ggtccccatg actctgcccg gggtgggatg atcccacatc ctcagtcccg ggacccttc | 600 |
| ccaacttgcc agctgaagtc tgagctggac atgctggttg gcaagtgccg ggaggaaccc | 660 |
| ttggaaggtg atatgtccag ccccaactcc acaggcatac aggatcccct gttggggatg | 720 |
| ctggatgggg gaggacct cgagagagag gagaagcgtg agcctgaatc tgtgtatgaa | 780 |
| actgactgcc gttgggatgg ctgcagccag gaatttgact cccaagagca gctggtgcac | 840 |
| cacatcaaca gcgagcacat ccacgggggag cggaaggagt tcgtgtgcca ctgggggggc | 900 |
| tgctccaggg agctgaggcc cttcaaagcc cagtacatgc tggtggttca catgcgcaga | 960 |
| cacactggcg agaagccaca caagtgcacg tttgaagggt gccggaagtc atactcacgc | 1020 |
| ctcgaaaacc tgaagacgca cctgcggtca cacacgggtg agaagccata catgtgtgag | 1080 |
| cacgagggct gcagtaaagc cttcagcaat gccagtgacc gagccaagca ccagaatcgg | 1140 |
| acccattcca atgagaagcc gtatgtatgt aagctccctg gctgcaccaa acgctataca | 1200 |
| gatcctagct cgctgcgaaa acatgtcaag acagtgcatg gtcctgacgc ccatgtgacc | 1260 |
| aaacggcacc gtggggatgg ccccctgcct cgggcaccat ccatttctac agtggagccc | 1320 |
| aagagggagc gggaaggagg tcccatcagg aggaaagca gactgactgt gccagagggt | 1380 |
| gccatgaagc cacagccaag ccctgggggcc cagtcatcct gcagcagtga ccactccccg | 1440 |

```
gcagggagtg cagccaatac agacagtggt gtggaaatga ctggcaatgc aggggggcagc   1500 actgaagacc tctccagctt ggacgaggga ccttgcattg ctggcactgg tctgtccact   1560
cttcgccgcc ttgagaacct caggctggac cagctacatc aactccggcc aatagggacc   1620
cggggtctca aactgcccag cttgtcccac accggtacca ctgtgtcccg ccgcgtgggc   1680
cccccagtct ctcttgaacg ccgcagcagc agctccagca gcatcagctc tgcctatact   1740
gtcagccgcc gctcctccct ggcctctcct ttcccccctg gctccccacc agagaatgga   1800
gcatcctccc tgcctggcct tatgcctgcc cagcactacc tgcttcgggc aagatatgct   1860
tcagccagag ggggtggtac ttcgcccact gcagcatcca gcctggatcg gataggtggt   1920
cttcccatgc ctccttggag aagccgagcc gagtatccag gatacaaccc caatgcaggg   1980
gtcacccgga gggccagtga cccagcccag gctgctgacc gtcctgctcc agctagagtc   2040
cagaggttca agagcctggg ctgtgtccat accccaccca ctgtggcagg gggaggacag   2100
aactttgatc cttacctccc aacctctgtc tactcaccac agccccccag catcactgag   2160
aatgctgcca tggatgctag agggctacag gaagagccag aagttgggac ctccatggtg   2220
ggcagtggtc tgaaccccta tatggacttc ccacctactg atactctggg atatggggga   2280
cctgaagggg cagcagctga gccttatgga gcgaggggtc caggctctct gcctcttggg   2340
cctggtccac ccaccaacta tggccccaac ccctgtcccc agcaggcctc atatcctgac   2400
cccacccaag aaacatgggg tgagttccct tcccactctg ggctgtaccc aggccccaag   2460
gctctaggtg gaacctacag ccagtgtcct cgacttgaac attatggaca agtgcaagtc   2520
aagccagaac agggggtgccc agtggggtct gactccacag gactggcacc ctgcctcaat   2580
gcccacccca gtgagggggcc cccacatcca cagcctctct tttcccatta cccccagccc   2640
tctcctcccc aatatctcca gtcaggcccc tatacccagc cacccccctga ttatcttcct   2700 tcagaaccca ggccttgcct ggactttgat tcccccaccc attccacagg gcagctcaag   2760
gctcagcttg tgtgtaatta tgttcaatct caacaggagc tactgtggga gggtgggggc   2820
agggaagatg cccccgccca ggaaccttcc taccagagtc ccaagtttct gggggggttcc   2880 caggttagcc caagccgtgc taaagctcca gtgaacacat atggacctgg ctttggaccc   2940
aacttgccca atcacaagtc aggttcctat cccacccctt caccatgcca tgaaaatttt   3000 gtagtgggggg caaatagggc ttcacatagg gcagcagcac cacctcgact tctgccccca   3060
ttgcccactt gctatgggcc tctcaaagtg ggaggcacaa accccagctg tggtcatcct   3120
gaggtgggca ggctaggagg gggtcctgcc ttgtaccctc ctcccgaagg acaggtatgt   3180
aaccccctgg actctcttga tcttgacaac actcagctgg actttgtggc tattctggat   3240 gagcccagg ggctgagtcc tcctccttcc catgatcagc ggggcagctc tggacatacc   3300
ccacctccct ctgggccccc caacatggct gtgggcaaca tgagtgtctt actgagatcc   3360
ctacctgggg aaacagaatt cctcaactct agtgcctaaa gagtagggaa tctcatccat   3420
cacagatcgc atttcctaag gggtttctat ccttccagaa aaattgggggg agctgcagtc   3480 ccctgcacaa gatgccccag ggatgggagg tatgggctgg gggctatgta tagtctgtat   3540
acgttttgag gagaaatttg ataatgacac tgtttcctga taataaagga actgcatcag   3600
```